United States Patent [19]

Rühland

[11] Patent Number: 4,655,740
[45] Date of Patent: Apr. 7, 1987

[54] AUTOTRANSFUSION APPARATUS

[76] Inventor: Dieter Rühland, Städtisches Krankenhaus, DE-7700 Singen, Fed. Rep. of Germany

[21] Appl. No.: 860,222

[22] PCT Filed: Aug. 6, 1985

[86] PCT No.: PCT/EP85/00396
§ 371 Date: Mar. 31, 1986
§ 102(e) Date: Mar. 31, 1986

[87] PCT Pub. No.: WO86/01116
PCT Pub. Date: Feb. 27, 1986

[30] Foreign Application Priority Data
Aug. 9, 1984 [DE] Fed. Rep. of Germany ....... 3429298

[51] Int. Cl.$^4$ .......... A61M 1/02; A61M 5/14
[52] U.S. Cl. .................. 604/4; 128/DIG. 3; 604/319; 604/320; 604/321
[58] Field of Search .................. 604/4–6, 604/319–321; 128/DIG. 3; 422/44

[56] References Cited

U.S. PATENT DOCUMENTS

| 3,965,896 | 6/1976 | Swank | 604/4 |
| 4,006,745 | 2/1977 | Sorenson et al. | 604/4 |
| 4,033,345 | 7/1977 | Sorenson et al. | 604/4 |
| 4,493,705 | 1/1985 | Gordon et al. | 604/122 |
| 4,564,359 | 1/1986 | Rühland | 604/4 |

FOREIGN PATENT DOCUMENTS 0072738 2/1983 European Pat. Off.
2346238 10/1977 France.

Primary Examiner—C. Fred Rosenbaum
Assistant Examiner—Gene B. Kartchner
Attorney, Agent, or Firm—Tarolli, Sundheim & Covell

[57] ABSTRACT

An apparatus for the autotransfusion of blood or similar body fluid. The apparatus includes a container which is an evacuable, vacuum-stable container having a bottom part and a cover part. The container also includes an inlet opening for the body fluid arranged in the cover part. An outlet opening for the body fluid is arranged in the cover part with a screen covering the outlet opening. An opening is arranged in the bottom part for the production of a gas flow connection to a chamber with a gas pressure different from that of the inside of the container. A membrane deformable by pressure, and through which the body fluid cannot pass is held at the edge between the bottom and the cover parts. The membrane divides the container into a gas-filled bottom chamber and a cover chamber sealed off from the latter to receive the body fluid. A float seals off the outlet opening.

17 Claims, 4 Drawing Figures

AUTOTRANSFUSION APPARATUS

BACKGROUND OF THE INVENTION

The present invention relates to an autotransfusion apparatus for blood or similar body fluids.

In operations such as heart surgery, vascular surgery, accident surgery or orthopedics, great and rapid losses of the patient's blood often occur. The loss of blood is usually compensated for with donated blood. However, donated blood may transmit diseases such as hepatitis. Moreover, several week old donated blood often lacks the elements of coagulation (coagulation factors and blood platelets) which are destroyed by storage. Therefore, an apparatus is needed which can recover blood entering the body cavities during an operation, and return it to the patient in order to reduce the use of donated blood and retain a large portion of the blood coagulation elements.

Complicated, expensive heart-lung machines are available today for major heart operations. The machine recovers the patient's own blood, pumps it through a pumping mechanism, and returns it to the patient through long hoses. Other kinds of machines collect the blood, isolate and wash the red blood cells and return the washed blood cells to the body. In both kinds of machines, the delicate blood cells are damaged by traveling through long tubes. In the second kind of machine, all the coagulation elements and the blood plasma are removed through the washing process. These machines are also relatively expensive and only available in a few locations.

Other devices have been developed for autotransfusion during operations. U.S. Pat. No. 4,047,526 discloses an autotransfusion system in which the blood is first drawn by vacuum into a hard container and then transferred into a bellows detachably connected at the bottom of the hard container. A vacuum can be produced by the bellows through which the vacuum in the hard container can be overcome. The bellows, filled with blood, is then detached from the hard container and then used to return the blood to the patient.

U.S. Pat. No. 4,033,345 discloses an autotransfusion apparatus with a rigid two-chamber system. An inner deformable bag is connected through a recoil valve with an upper chamber which first collects the blood. The blood can be actively transfused back into the patient through another opening within the recoil valve and filtering units by pressurizing the space between a hard second chamber and the outer surface of the bag. The conduction of the blood from the rigid collection container into the flexible bag takes place through alternate application of pressure and vacuum.

Another autotransfusion device disclosed in German Disclosure No. 32 18 561 includes a device corresponding to the second chamber of the U.S. Pat. No. 4,033,345, mentioned above. However, the blood must be suctioned out, without a recoil valve, through an opening in the under side of the chamber. A screen or a similar blood filter cannot be used with this device.

U.S. Pat. No. 4,014,329 discloses another two-chamber autotransfusion device in which the first chamber operates by the same principle as was described in U.S. Pat. No. 4,033,345 for the second chamber. However, the blood flows out, by gravity, at the under side of the chamber into the second chamber with a filter.

With these known autotranfusion devices it is possible, of course, to collect the blood occurring during the operation and to retransfuse it to the patient. However, they have a number of serious disadvantages. In the multi-chamber systems, the blood comes in contact with a large surface area, which effects a harmful activation of coagulation and traumatizing of the blood. There also takes place a further traumatizing, harmful to the delicate blood cells, in the transfer from one into the other chamber, especially when recoil valves are used between the chambers.

If the blood is suctioned from below into the vacuum chamber, the blood already accumulated in the apparatus is set in turbulent motion by subsequently suctioned blood, while air carried along, and coarse components, such as blood clots, fat cells and bone splinters, cause a considerable foam forming as well as traumatizing of the blood cells. In the absence of course filters to hold back substances carried along in the blood, there exists in the conventional fine filters provided on the transfusion instruments, a latent danger of stoppage. Moreover, blood collection chambers provided with inlet and outlet openings on the cover and bottom side, require a considerable construction height, in view of the necessary volume of blood to be suctioned, which is usually higher than the very small sterile operation zone on the patient. Therefore, in the known autotransfusion devices, there are usually problems of sterility in the sterile operation area, which can only be compensated by setting up the autotransfusion apparatus outside the sterile zone, at the cost of a longer suction distance. In this way, a higher suction pressure is necessary and there is an increased contact with foreign substances, both of which mean an additional trauma for the blood. In two chamber systems, the conduction of the large quantity of blood, after aspiration, into the second chamber, requires time, which neither the anaesthetist nor the surgeon has available. The time factor is especially harmful to the patient also, since in this case, he needs the blood back quickly.

These problems have been solved by the autotranfusion device disclosed in German Patent Application No. P 33 04 486.4. However, the problem of the air present in the autotransfusion apparatus along with the blood has remained unsolved. Before the infusion of the collected blood, the air must be removed to prevent an air embolism. The autotransfusion device can only be used so long as no air can be infused into the patient.

SUMMARY OF THE INVENTION

The present invention is an autotransfusion apparatus for rapidly collecting blood over a short distance without damage, and without the danger of air embolism, transfuse it back into the patient. In particular, the surfaces contacted by the blood are small, foam forming is avoided, and of a low construction height which permits use in the sterile area of the patient.

The present invention includes both the blood inlet opening and the blood outlet opening in the cover part of a single blood collection chamber. A coarse filter is connected before the outlet. A sealing float is also connected before the outlet. The suctioned blood flows from above into the chamber and flows downward along the chamber wall without foam formation. In retransfusion, the apparatus is inverted and the blood flows, filtered, through gravity and/or increased gas pressure in bottom chamber, separated by a membrane from the blood collection chamber, back to the patient. The sealing float automatically closes the outlet opening as soon as all the blood has run out. The preceding blood suction is effected through vacuum, which is applied, either (in the case of bottom chamber closed gastight) at the outlet opening, or (in case of outlet opening closed gastight) in the bottom chamber. The membrane is fastened only at its single edge between the bottom and cover parts. The size ratio between bottom and cover parts is unimportant and need only assure that the membrane can be applied as widely as possible, alternately, both to the wall of the bottom part and that of the cover part, so that, alternately, the bottom and the cover chambers have a minimal residual volume.

The inlet and outlet openings, with use of vacuum in the cover chamber, must be far enough apart to prevent a transfer of blood into the applied vacuum source.

The autotransfusion apparatus according to the invention has a number of important advantages: The blood is collected in a single chamber without narrowed cross section and without formation of foam, under controlled producible pressure, and pre-filtered, from the same chamber, with the use of a free preset pressure, infused, at the desired speed, directly into the patient, without at the end of the infusion, any air, present with the blood, being able to get into the blood vessel of the patient. Only a very slight construction height of the vacuum-stable container is necessary so that it can be handled at any time in the sterile area of the operation. Moreover, sealing problems near the three continer openings and in connection with the membrane, are prevented by the fact that these openings are all arranged in the substantially rigid wall of the cover or bottom part, and therefore independent of the sealing edge of the membrane. Therefore, only the rim of the membrane need be held fast, in the functionally most suitable way, between the cover and bottom parts, while passage openings with hose connections, within the membrane surface, are eliminated. Thus, the membrane properties and the sealing of the membrane can be chosen especially functional and freely chosen, independently of the inlet and outlet openings.

Suitable embodiments of the subject invention, which assure, in particular, a good sealing effect of the float, as well as a simple handling of the autotransfusion apparatus, and prevent, in the best possible way, damage to the blood and to the patient, are contained in further claims.

BRIEF DESCRIPTION OF THE DRAWINGS

Other details, features and advantages of the present invention will become apparent to one skilled in the art upon a reading of the description which follows, made with reference to the respective drawings, in which one preferred form of execution of an autotransfusion apparatus according to the invention has been represented, in which.

DESCRIPTION OF A PREFERRED EMBODIMENT

Figure 1:
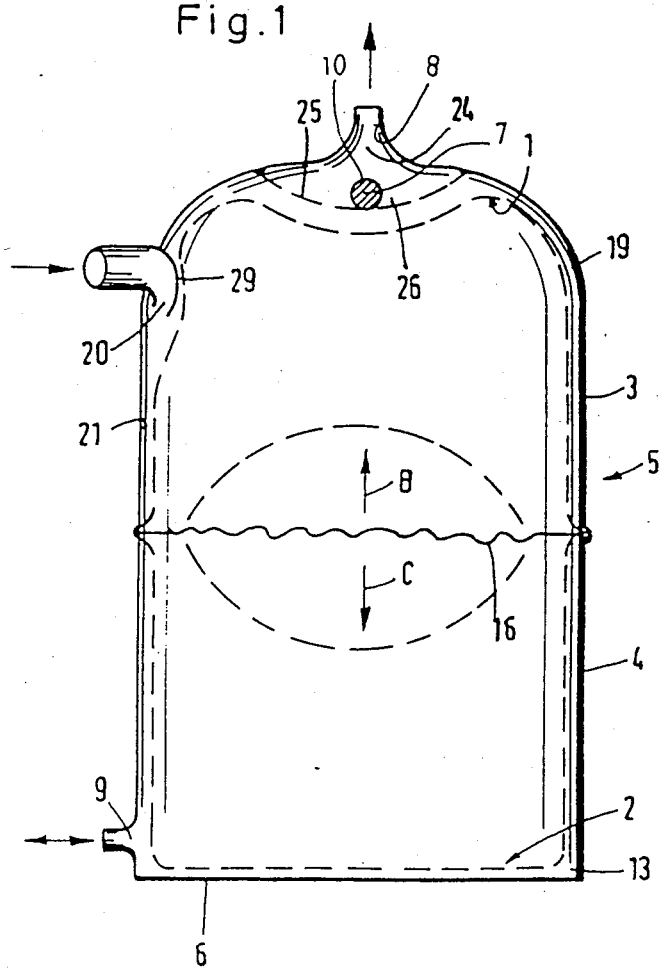
FIG. 1 is a side view, partly in section, of the present invention.

FIG. 1 illustrates the essential parts of an autotransfusion apparatus in the form of a container 5 consisting of sterilized plastic or glass designed as a one-time use container. The container 5 has a cylindrical or rectangular cross section and consists of a bottom part 4, and a cover part 3 which are connected fluid tight. The container 5 is vacuum-stable and can be evacuated through an outlet opening 24 in the cover part 3 or an opening 9 in the bottom part 4. In the cover part 3 an inlet opening 20 is arranged at a sufficient distance from the outlet opening 24 near a trumpet-shaped mouthpiece 29 and tangent to the inner wall 21 of the cover part 3, so that body fluid suctioned from the patient runs toward this inner wall by gravity, without the formation of foam. A screen 25, to hold back coarse substances carried along in the blood, covers the outlet opening 24 at a distance from the inner chamber of the container. The opening 9 can be closed gas-tight, and makes possible, after the removal of the closing, the penetration of atmospheric air or compressed air into the inside of the container. A membrane 16, deformable by pressure and through which body fluid cannot pass, is held fast, gas-tight, between the bottom part 4 and the cover part 3, at its edge, so that it divides the container 5 into a gas-filled bottom chamber 13, and a cover chamber 19, sealed off from the latter, to receive the body fluid. Under the influence of a fluid pressure the membrane 16, as shown in broken line, can lie mostly against the inner contour 1 of the cover part 3, and alternately, against the inner contour 2 of the bottom part 4. Naturally, all intermediate positions, between these two extreme positions, can be taken by the membrane 16, as represented by the other broken lines and arrows of direction, B and C. The joining between the rim of the membrane and the bottom 4 and cover 3 parts may be done by plastic welding, with formation of the one-piece, one-time use container.

With the container completely filled with blood, the membrane 16 takes substantially the form of the inner contour 2. Then the influx line from the patient is tightly closed or possibly clamped off at the patient side. After the removal of a vacuum line (not shown) which is connected either to the outlet opening 24 or the opening 9, by admitting compressed air through the opening 9, and connecting a retransfusion insert at the opening 24, the air still present in the cover chamber 3 and the system areas after it, can be driven out. After inverting the container 5, and after a period of time, all the light substances of the blood, such as air bubbles not yet driven out, and fat cells, have collected under the membrane 16 (then lying upward). With the subsequent admission of surrounding or compressed air through the opening 9, the blood flows back to the patient until the membrane 16 is applied wholly against the contour 1 of the cover part 3 and against the screen 25. With this, there remain between the membrane 16 and the screen 25 in the cover space 19, only the coarse components held back by the screen, while fine components, such as the said air bubbles or fat cells then collect, concentrated, in the space 26 between the outlet opening 24 and the screen and can no longer reach the patient.

A float 7 may be designed as a ball and arranged between the outlet 24 and the screen 25. The spherical surface forms here the sealing surface 10, on the float side, and the inner surface of the cover part 3, surrounding the outlet opening 24, forms the container-side sealing surface 8 for the float. The sealing surface 8 is preferably designed conical and converges in the direction of the outlet opening 24.

The float 7 should have great enough bouyancy in the body fluid to be transfused, so that it will not remain stuck, by adhesion or the like, against the parts of the container 5 surrounding it, when the fluid level rises or falls. The float 7 should therefore have enough bouyancy so that it always floats on the body fluid. This can be attained especially with hollow floats. On the other hand, the bouyancy of the float should not be so great that the float, in evacuation of the cover chamber 19, can be lifted by the evacuating stream of gas, so that the evacuating stream of gas is interrupted. At least the surface 10 of the float should consist of a material harmless to blood, such as PTFE (Teflon), polyurethane or a silicone. For example, a suitably formed piece of cork or the like may provide for the buoyancy of the float 7, while a coating of material harmless to blood forms the sealing surface 10 of the float.

Figure 2:
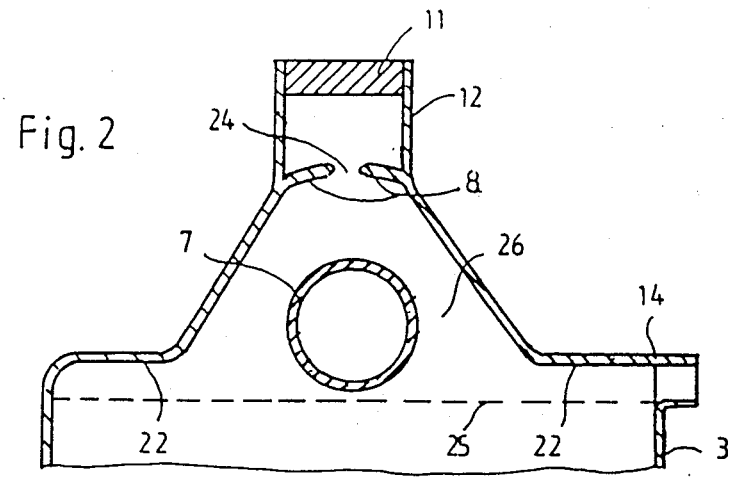
FIGS. 2–4 are enlarged cross sectional views of a portion of the cover part of the apparatus in FIG. 1.
Figure 3:
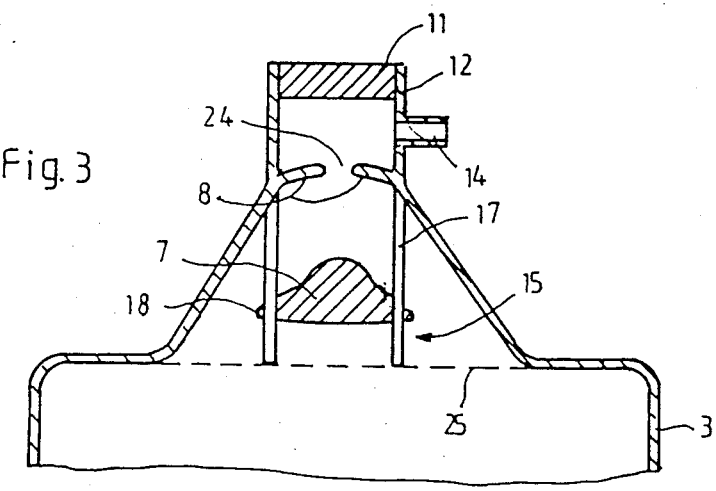
Figure 4:
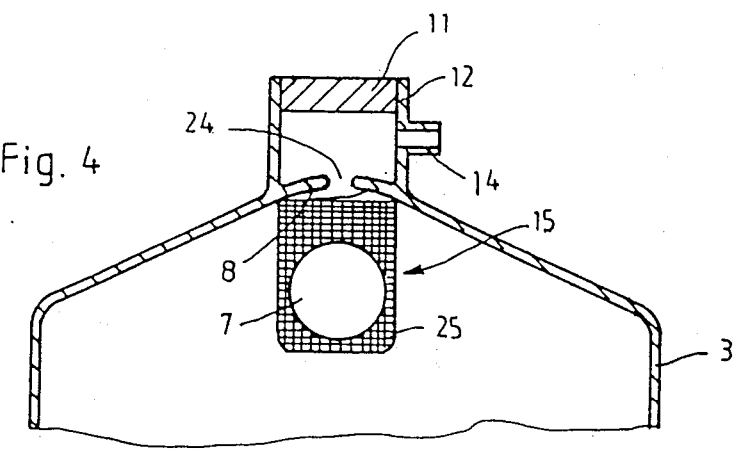

Embodiments of the cover part 3 of the autotransfusion apparatus illusted in FIGS. 2 to 4, may have outlet openings 24 arranged after a blood outlet 12 and closed with a piercing membrane 11. Such piercing membrane, for injection needles and the like, are widely used in applied medical technology and therefore need not be described in detail.

Accordings to FIGS. 3 and 4, the outlet opening 24 may be arranged after an evacuation connection 14, independent of the blood outlet 12. This has the advantage that in suctioning the body fluid, the latter cannot get into the vacuum pump, because the float 7 floats on the body fluid already suctioned in, and closes the outlet opening 24 as soon as the cover chamber 19 and the chamber situated above the screen 5, thus, the whole container 5 is filled with body fluid.

Moreover, according to FIGS. 3 and 4, the outlet opening 24 may be surrounded by a float-capturing cage 15. This serves for a secure guiding of the float just before it reaches the sealing surface 8 on the outlet opening 24. For example, projections on the inside of the cover 3 as float-capturing cage are suitable, of which the float-side end edges can guide the float in the direction of the outlet opening 24. According to FIG. 3, a float-capturing cage may also consist of several rods 17, which extend between the inner surface of the cover part and the screen 25. In particular, the float 7 may have guide elements 18 at the rim, such as eyelets, grooves or the like, which correspond with the rods 17 and make possible an easy sliding guiding of the float 7. This kind of guiding is especially suitable for floats, illustrated in FIG. 3, varying from the spherical form. But the float-catching cage 15 may also consist, by proper shaping and arangement of the screen 25, as illustrated in FIG. 4, of the screen 25 itself.

According to FIG. 2, there may be provided, between the screen 25 and the outlet opening 24, an offset 22 in the cover part. In this way, the screen 25 is given as great as possible an effective surface, without the space 26 beneath being unnecessarily great. Namely, it is desirable, for the proper sealing function of the float 7, that the side walls of the chamber 26 in the cover part 3, leading to the outlet opening 24, be sufficiently sloped in order to improve the guiding of the float 7. The evacuation connection 14 may also be provided in the area of this offset 22. A closing of this evacuation connection 14, by the float 7, which in FIG. 2 is designed as a hollow ball, is prevented by a proper dimensioning of the distance between the screen 25 and the offset 22. This distance should be less than the diameter of the float. The ball form has proved an especially advantageous outer contour for the float 7. In the individual case, a flattened ball or a disc-form float, perhaps with a special sealing surface addition, as in FIG. 3, might also be advantageous.

Having described a preferred embodiment, I claim:

1. An autotransfusion apparatus for blood or similar body fluid, consisting of:
    a vacuum-stable container having a bottom part and a cover part, said cover part including an inlet opening for the body fluid, and an outlet opening for the body fluid, a screen covering said outlet opening, said bottom part including an opening connectible with means for producing a gas pressure in the interior of said container;
    a membrane impermeable by the body fluid, and deformable by said gas pressure and fastened gas-tight at the edge between said bottom and cover parts, said membrane divideing the container into a gas-filled bottom chamber and a cover chamber, said cover chamber being sealed from said bottom chamber to receive the body fluid; and
    a float buoyant in the body fluid for sealing said outlet opening when said container empties.

2. An apparatus according to claim 1 wherein said float is disposed between said outlet opening and said screen.

3. An apparatus according to claim 2 wherein said outlet opening is formed by a conical sealing surface.

4. An apparatus according to claim 1 wherein said float has a spherical sealing surface.

5. An apparatus according to claim 1 wherein said outlet opening is disposed after a blood outlet closed with a piercing membrane.

6. An apparatus according to claim 5 wherein said outlet opening is disposed after an evacuating connection independent of said blood outlet.

7. An apparatus according to claim 1 further including a float-enclosing case surrounding said outlet opening.

8. An apparatus according to claim 2 further including an offset disposed between said screen and said outlet opening in said cover part.

9. An apparatus according to claim 1 wherein said sealing surface of the float consists of a material harmless to blood.

10. An apparatus according to claim 1 wherein said float has the form of a ball.

11. An apparatus according to claim 1 wherein said membrane under the influence of fluid pressure can be laid both against an inner surface of the cover and also against an inner surface of the bottom part.

12. An apparatus according to claim 1 wherein said container with said membrane may be designed as a one-piece, one-time use container of plastic.

13. An apparatus according to claim 1 wherein said cover part is fastened detachably to said bottom part.

14. An apparatus according to claim 13 wherein a rim section of said membrane is clamped between said cover and bottom parts.

15. An apparatus according to claim 1 wherein said inlet opening discharges tangential to the inner wall of the cover part.

16. An apparatus according to claim 15 wherein said inlet opening consists of a mouthpiece widened trumpet-like.

17. An apparatus according to claim 1 wherein said screen is detachably held at a distance before the outlet opening and defines a chamber for the holding back of substances floating on the body fluid and carried along through said screen.

* * * * *